United States Patent
Van Wijk et al.

(10) Patent No.: US 6,423,262 B1
(45) Date of Patent: Jul. 23, 2002

(54) TECHNIQUE FOR MEASURING PROPERTIES OF POLYMERIC FIBRES

(75) Inventors: Robert Jan Van Wijk, Arnhem; Anton Peter De Weijer, Nijmegen; Dirk Albert Klarenberg, Dieren; Roel De Jonge; Gert Jan Jongerden, both of Velp, all of (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/486,588

(22) PCT Filed: Aug. 24, 1998

(86) PCT No.: PCT/EP98/05490

§ 371 (c)(1),
(2), (4) Date: May 1, 2000

(87) PCT Pub. No.: WO99/12019

PCT Pub. Date: Mar. 11, 1999

(30) Foreign Application Priority Data

Sep. 1, 1997 (NL) .............................................. 1006895
Oct. 17, 1997 (NL) ............................................ 1007300

(51) Int. Cl.$^7$ ......................... G01N 21/65; G01N 21/89

(52) U.S. Cl. ...................................... 264/408; 264/409

(58) Field of Search ................................. 264/408, 409

(56) References Cited

FOREIGN PATENT DOCUMENTS

| DE | 36 39 636 A1 | 5/1988 |
|----|--------------|--------|
| EP | 0 637 742 A1 | 2/1995 |
| EP | 0 781 990 A1 | 7/1997 |
| WO | WO 87/06011 A1 | 10/1987 |
| WO | WO 91/11695 A2 | 8/1991 |

OTHER PUBLICATIONS

E. Steven Brandt, Analysis Of Spectural Sensitizing Dyes In Photographic Films By Enhanced Raman Scattering Spectroscopy, Analytical Chemistry, vol. 61, No. 5, pp. 391–398, Mar. 1989.

D.A. Gilmore et al., Qunatitative Detection Of Environmentally Important Dyes Using Diode Laser/Fiber–Optic Ramm Spectroscopy, Applied Spectroscopy, vol. 49, No. 4, pp. 508–512, Apr. 1995.

J. S. Church et al., New Cell For The Fourier Transform Raman Analysis Of Fiber And Textile Samples, Applied Spectroscopy, vol. 48, No. 7, pp. 813–817, Jul. 1994.

J. F. Aust et al., Novel In Situ Probe for Monitoring Polymer Curing, Applied Spectroscopy, vol. 50, No. 3, pp. 382–387, 1996.

I. De Wolf, Micro–Raman Spectroscopy To Study Local Mechanical Stress In Silicon Integrated Circuits, Semiconductor Science and Technology, vol. 11, No. 2, pp. 130–154, Feb. 1996.

B. Arjyal et al., Stress/Strain Measurements In Advanced Composites Using Remote Laser Raman Microscopy, Nondestructive Testing And Evaluation, vol. 12, pp. 355–366, 1996.

C. Galiotis, Laser Raman Spectroscopy, A New Stress/Strain Measurement Technique For The Remote And On–Line Nondestructive Inspection Of Fiber Reinforced Polymer Composites, Materials Technology, vol. 8, No. 9–10, pp. 203–206, Sep. 1993.

Primary Examiner—Leo B. Tentoni
(74) Attorney, Agent, or Firm—Oliff & Berridge, PLC

(57) ABSTRACT

The invention pertains to a technique for determining the dye uptake or measuring one or more structural parameters or mechanical properties of polymeric fibres. This technique entails measuring the Raman spectrum of the fibres during or after a spinning process. After the Raman spectrum has been treated, a model is applied to it which is derived from the Raman spectra of fibres having the same chemical composition as the fibres to be examined.

10 Claims, 2 Drawing Sheets

TECHNIQUE FOR MEASURING PROPERTIES OF POLYMERIC FIBRES

FIELD OF THE INVENTION

The invention pertains to a technique for measuring one or more structural parameters or mechanical properties of polymeric fibres, or for determining their dye uptake.

BACKGROUND

When spinning polymeric fibres from a polymeric melt or from a solution, the melt or solution is extruded through a spinneret. Next, the formed fibres are cooled and/or washed and, optionally, drawn to produce fibres or a yarn having properties which render said fibres pre-eminently suitable for textile or technical application.

Examples of different spinning processes are to be found, e.g., in Fundamentals of Fibre Formation (The science of Fibre Spinning and Drawing), A. Ziabicki, Wiley Interscience Publication, London, 1976, or in Synthesefasern (Grundlagen, Technologie, Verarbeitung und Anwendung), B. von Falkai, Verlag Chemie, Weinheim, 1981.

On conclusion of the spinning process the formed fibres are wound or collected in some other way, and the mechanical properties and structural parameters of the fibres are measured.

The measuring of the properties of the fibres takes place under carefully controlled temperature and atmospheric humidity conditions, according to fixed procedures, this in order to enable comparison of the results of different measurements. Generally, such measurements are carried out in a laboratory specially equipped for the purpose. In consequence, it is impossible to make use of the result of these measurements during the actual spinning process, e.g., to select fibres having particular properties, such as a certain breaking tenacity, elongation at break or level of shrinkage, or for their suitability for dye uptake.

A well-known, long-used method of determining the dye uptake of textile fibres is to employ a comparative test in which various fibre samples have their different uptakes of a standard dye determined. To this end small pieces of yarn of different samples are knitted into hose. Next, the hose is dyed with a dye critical to the material under critical conditions, i.e., the time during which the knitted hose is contacted with the liquid in which the dye is dissolved is too short to effect full saturation of the hose with dye or complete uptake of the dye from the bath. In addition, such a test employs dyes which have a slow uptake by the fibrous material in question, and the determination is carried out at a comparatively low temperature. The dye uptake is then evaluated visually by indicating whether a yarn sample's dye uptake is superior, inferior or normal as compared with that of an adjoining yarn sample.

Major drawbacks of this known method are that:
- the results obtained are relative
- the determination is dependent on the person carrying out the test
- the method is complex and time-labour-intensive
- only comparatively large differences in dye uptake can be made visible.

Admittedly, it is possible to remove the subjective elements present in this determination by using photometric equipment (e.g., a HunterLab spectrometer), but in that case the knitted structure of the hose is found to have a major effect on the determination.

Figure 1:
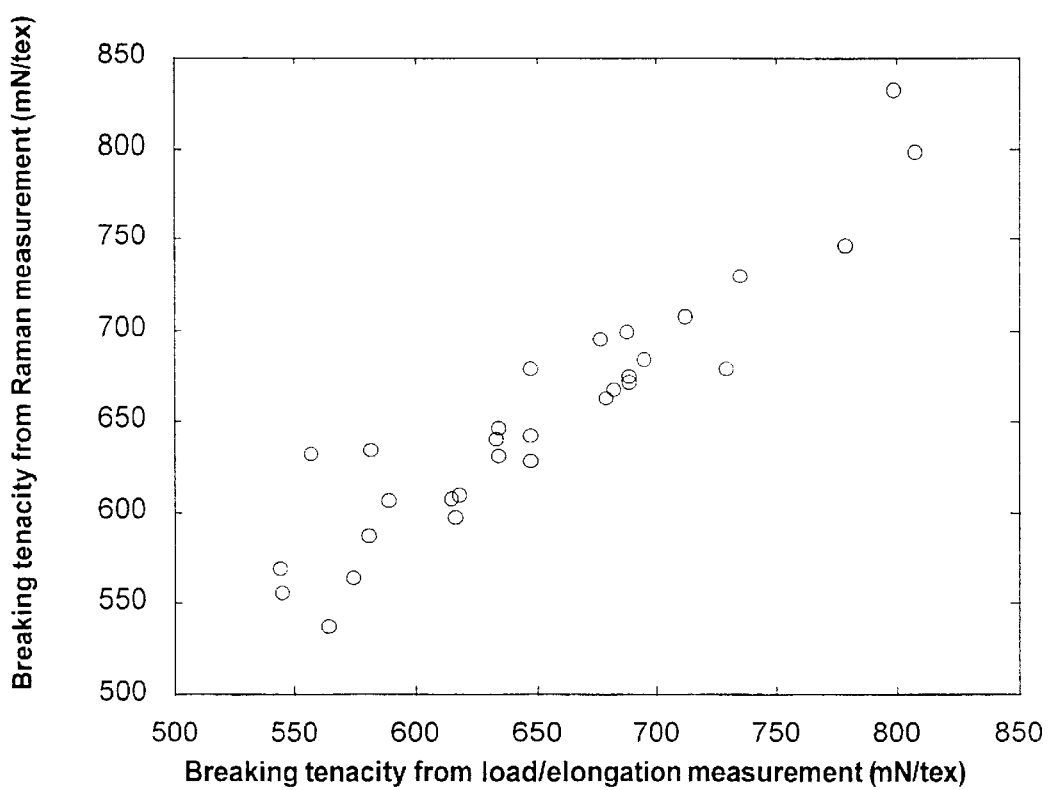
FIG. 1 shows the breaking tenacity value measured on the respective samples in a load/elongation experiment plotted against the value determined by means of the Raman spectrum according to Example 2.

Accordingly, there is great need for a technique which allows the mechanical and/or structural properties of the formed fibres to be made available during or shortly after the spinning process, as well as for a method of swiftly and simply determining the dye uptake of textile fibres in such a manner as will enable an absolute comparison to be made among fibre samples.

The technique according to the invention now provides a process which satisfies the aforementioned requirements.

The invention concerns a technique for measuring one or more structural parameters or mechanical properties of polymeric fibres or for determining their dye uptake, said technique being comprised of the following steps:

a) creating a model to determine one or more structural parameters or mechanical properties or the degree of dye uptake from a measured Raman spectrum of fibres having the same chemical composition as the fibres to be examined, b) measuring a Raman spectrum of the fibres to be examined by irradiating the fibres with high-intensity monochromatic light, capturing the scattered light, and passing the scattered light to a light-sensitive sensor, c) treating the measured spectrum obtained in step b), and d) applying the model obtained via step a) to the treated spectrum obtained in step c) in order to arrive at a value of the respective structural parameters or mechanical properties of the fibres to be examined, or to determine their dye uptake.

In this patent application the term "fibres" refers to staple fibres, short fibres, and filaments as well as yarns (an assembly of filaments).

The technique according to the invention is not susceptible to the shape of the fibrous material present. Thus it is possible to measure the structural parameter(s) and/or mechanical property/properties and to determine the dye uptake of a collection of short fibres as well as staple fibres, of non-transparent as well as dull fibrous material, and of fibrous material which has been wound or has undergone additional processing. It does not make any difference either whether the fibres have been incorporated into a fabric or a non-woven.

The only condition which should be placed upon the fibrous material present is that there is a sufficient amount of it to measure an accurate Raman spectrum with the aid of the scattered light in a reproducible manner. If only a small amount of fibrous material is available, this means that a longer measuring time will have to be selected to enable sufficiently accurate Raman spectrum measurement.

The technique according to the invention is susceptible neither to the chemical composition of the polymeric fibres nor to the manner in which the polymer is spun. The technique thus can be used when meltspinning thermoplastic polymers, such as polyester, polyamide, polyolefin, and alternating co-polymers of carbon monoxide and olefins, so-called polyketones. The technique can also be used when spinning from a polymeric solution, e.g., when spinning from a solution containing cellulose, (aromatic) polyamides, polyketones, (aromatic) polyesters or polyolefins.

The skilled person will be familiar with various ways of making high-intensity monochromatic light available. In the determination according to the invention it is preferred to use monochromatic light generated with the aid of a laser, since such light is monochromatic and, depending on the laser's power, of high intensity as well.

When selecting the wavelength of the light used to irradiate the fibrous material, two different phenomena should be taken into account, viz. attenuation of the intensity of the scattered light as the wavelength of the irradiating light increases, and luminescence phenomena exhibited by the fibrous material under the influence of the irradiation. Both phenomena are objectionable in that they have a negative effect on the accuracy of the determination. The decreasing intensity of the scattered light (i.e. the Raman signal) is approximately proportional to $1/\lambda^4$, with $\lambda$ being the wavelength of the irradiating light. The wavelength regions in which luminescence phenomena occur are dependent on the chemical composition of the fibrous material. Thus when irradiating most fibrous materials a too strong attenuation of the scattered light is found when the wavelength of the light is more than 900 nm, while a strong luminescence is found when the wavelength of the light is less than 600 nm. In the case of most fibrous materials when using a simple dispersive Raman spectrometer an optimum in the range of 600 to 900 nm is found for the wavelength region of the irradiating light.

Alternatively, the fibrous material can be irradiated with light having a wavelength of more than 900 nm. In that case, however, detecting the scattered light will require special equipment (FT Raman spectrometer) which at present is suitable for use only under laboratory conditions.

In the process according to the invention a portion of the scattered light is captured, e.g., with the aid of a lens, and the light is filtered off at the irradiation wavelength of the fibrous material. The scattered, filtered light is then passed to a light-sensitive detector so coupled to peripheral equipment that a Raman spectrum can be recorded. To enable simultaneous measurement of a portion of the spectrum, the light preferably is passed to the light-sensitive detector via a dispersive medium (for wavelength separation of the scattered light). Examples of a dispersive medium suitable for use in this process are a prism and a lattice, more particularly a holographic lattice. As light-sensitive detector may be used, e.g., a CCD-camera or a photomultiplier. It is well-known to the skilled person how these different members should be interconnected to record a Raman spectrum. Preferably, in view of wavelength resolution and sensitivity to light, use is made of a holographic lattice in combination with a CCD-camera.

It is of great importance to have the wavelength of the monochromatic light used to irradiate the fibrous material precisely known. Also, it is of great importance to have the wavelength scale of the equipment used to record the Raman spectrum properly calibrated.

In a favourable process according to the invention use is made of compact and interference-free dispersive mediums and light-sensitive detectors, this with a view to the invention's employment in the large-scale production of fibrous material.

In an especially favourable process an assembly of equipment is used to generate the laser beams and measure the Raman spectrum. One example of such an assembly of Raman equipment is the HoloProbe VPT System™ manufactured by Kaiser Optical systems, Inc. In such an assembly of equipment the laser light is passed from the assembly to the fibrous material to be measured, e.g., by means of a fibre optics cable, and the scattered (and filtered) light is passed from the fibrous material to the assembly, e.g., by means of a fibre optics cable, with the assembly also containing a dispersive medium, a light-sensitive sensor, and various devices for interconnecting these members.

For greater reproducibility of the results it is preferred to install the Raman equipment in a space where the temperature and the atmospheric humidity are kept within specified limits. In such a set-up the laser light and the reflected light can be passed to and from the fibrous material to be measured by means of optical (fibre optics) cables, since it is not required that the fibrous material to be measured is also present in a space where the temperature and the atmospheric humidity are kept within specified limits.

To determine the mechanical and/or structural properties of fibres it is sufficient when the obtained Raman spectrum exhibits a signal/noise ratio of more than 2000, with the noise being defined as the standard deviation from the differences between the spectra before and after "Wavelet smoothing" and the signal being the highest value in the wavelength region of 600–2000 cm$^{-1}$. In the case of "Wavelet smoothing" it is assumed that the Raman spectrum is built up of an information signal and a noise signal. The spectrum is modelled using a linear combination of so-called wavelet bases. These bases are orthonormal. The standard deviation from the difference between the measured spectrum and the information spectrum modelled using the wavelet bases is called noise. The signal/noise ratio is defined as the ratio of the highest peak in the information spectrum in the wavelength region of 600–2000 cm$^{-1}$ to the noise. Coiflet functions may serve as wavelet bases. For modelling the spectrum use may be made, e.g., of the waveshrink function with coiflet C12 of the statistical software package Splus and "soft thresholding." For a more detailed description of the mathematical operations employed reference may be had to D. Donoho and I. Johnstone, Ideal spatial adaptation by wavelet shrinkage (Technical Report, Department of Statistics, Stanford University, 1992), G. Strang and N. Truong, Wavelets and Filter Banks (Wellesley-Cambridge Press, 1996), and B. Walczak and D. L. Massart, Chemometrics and Intelligent Laboratory Systems, 36 (1997), 81–94.

To enable quantitative calculations to be made from a measured Raman spectrum, the measured spectrum has to undergo a number of treatment steps known, int. al., from chemometrics. These steps can be classified by their respective functions as preparation, scaling, data reduction, and calibration.

For each of these treatment steps several arithmetical operations are known, viz.

| Preparation | Scaling | Data reduction | Calibration |
| --- | --- | --- | --- |
| none | None | none | MLR |
| 1$^{st}$ derivative | Variance | PCA | PCR |
| 2$^{nd}$ derivative | Average | FSQ | PLS |
| filtering | Peak | Wavelength selection | ANN |
| averaging | Surface | Wavelet Tr. | PPREG |
| baseline correction | MSC | Extraction | |
| | | PLS components | |
| | | Averaging | | with

ANN=Artificial Neural Network

FSQ=Full Spectrum Quantisation

MLR=Multiple Linear Regression

MSC=Multiple Scattering Correction

PCA=Principal Component Analysis

PCR Principal Component Regression

PLS=Partial Least Squares
PPREG=Projection Pursuit Regression
Wavelet Tr.=Wavelet Transformation It proved possible, after carrying out some of the treatment steps mentioned above, to determine a number of mechanical properties and structural parameters of the unknown material using the found spectrum and comparing it with the spectra of known fibrous materials of the same chemical composition. For textile polyester a clear correlation was found between the density of the fibrous material and the dye uptake.

As a measure of the dye uptake may be selected the so-called dye uptake index (DI), which is defined as follows:

$$DI = \frac{D - D_{min}}{D_{max} - D_{min}} * 10$$

wherein
D=Density of the fibrous material measured from the Raman spectrum,
$D_{min}$=minimum density of the fibrous material, e.g., for PET fibrous material $D_{min}$=1355 kg/m$^3$,
$D_{max}$=maximum density of the fibrous material, e.g., for PET fibrous material $D_{max}$=1405 kg/m$^3$.

In order to be able to calculate a quantitative measure of the dye uptake or the desired mechanical or structural property from a found Raman spectrum, first the connection has to be established between the Raman spectra of a number of fibrous materials and their dye uptake or certain mechanical or structural properties. This collection of fibrous materials of which the dye uptake, the mechanical or stuctural properties, and the Raman spectrum are known is also called a calibration set.

This calibration set preferably is selected such that it contains all variations which may occur in the samples of which the mechanical and/or structural properties need to be quantified using the Raman spectrum. In actual practice, such a calibration set will consist of 20–100 samples.

In order to be able to use the calibration set for quantifying one or more mechanical and/or structural properties of the unknown samples, every sample of the calibration set has its Raman spectrum measured, as well as its dye uptake or the desired mechanical and/or structural properties.

For quantifying the dye uptake or one or more mechanical and/or structural properties preferably a Raman spectrum is recorded in the region of 600–2000 cm$^{-1}$ with a resolution $\leq 5$ cm$^{-1}$ and a signal/noise ratio higher than or equal to 2000, with the baseline of the spectrum being corrected for background radiation.

Different combinations of the above-mentioned chemometric treatment steps may be used to calculate one or more mechanical and/or structural properties of an unknown yarn sample using the measured Raman spectrum.

For instance, the measured data can be reduced and scaled by standardising the surface area underneath the measured spectrum in the wavelength region of 1600–1800 cm$^{-1}$ and calibrating the mechanical and/or structural properties of the calibration set and the reduced and scaled spectrum using PLS-1 analysis (a PLS analysis with one output variable), or PLS-2 analysis (a PLS analysis with more than one output variable). Repeated use of the data of 80% of the samples in the calibration set, with the samples for each validation being selected at random, makes it possible to employ the data of the remaining 20% of the samples for the validation of the model. This process is also known as "cross-validation."

In addition, the entire spectrum can be quantified using Fourier Transform analysis, in which process for the calibration of the spectrum (by means of PLS) use is made of the 60 lowest Fourier coefficients from the analysis. The above-described "cross-validation" of the model may also be employed in this method. Alternatively, the data in the measured spectra can be scaled and reduced by standardising the surface area of the spectrum in the entire wavelength region, in which process the data can be reduced further by the use of a principal components analysis (PCA), in which case the spectrum is calibrated using a multivariant analysis technique such as ANN. In this method also use may be made of the above-described "cross-validation" of the model.

It proved possible in the manner described above to determine from a measured Raman spectrum of a polymeric fibre a value for the mechanical properties and structural parameters which are determined by the fibre's molecular structure. Thus in the case of fibres obtained by meltspinning polyethylene terephthalate a value can be determined from the Raman spectrum for the breaking tenacity, the elongation at break, the initial modulus, the final modulus, and the shrinkage. In the case of fibres obtained by spinning a solution containing polyaramid and sulphuric acid, it is possible, e.g., to determine a value for the initial modulus from the Raman spectrum.

To determine the preciset possible value of one or more mechanical and/or structural properties from a measured Raman spectrum or to determine the dye uptake as accurately as possible therefrom, it is preferred to have the properties of the fibre samples used to create the model, the so-called calibration set, correspond as much as possible to the properties of the polymeric fibre to be measured. This means, e.g., that when this method is employed to determine one or more structural parameter(s) and/or mechanical property/properties or the dye uptake of drawn fibres, fibres having the same chemical composition and spun under comparable conditions are selected for the calibration set.

When creating the model and applying it to the treated spectrum of the polymeric fibre in question, generally the use of data from the spectral region between 600 and 2000 cm$^{-1}$ in the Raman spectrum will be satisfactory. In that case it is possible to opt for the use of a continuous spectral region between the two aforesaid limits. Alternatively, however, data from a number of spectral regions within the spectral region between 600 and 2000 cm$^{-1}$ may be employed.

The properties measured can be used to control the process. For instance, if a measurement carried out during the spinning of the fibre(s) or immediately after the collecting/winding of the spun fibre(s) shows that a particular property of the polymeric fibre no longer meets a pre-established criterion or there is a risk of its failing to do so, it is possible to adjust the spinning process in such a way that the property in question of the polymeric fibre once again satisfies the criterion concerned. Thus the measurement can be employed, e.g., to make fibres in a spinning process which have a breaking tenacity fluctuating within very narrow margins.

Alternatively, the measurement can be used to select fibres having particular properties. Determining the properties of the fibres produced on conclusion of a spinning process makes it possible to group or sort the produced fibres on the basis of these properties. Thus on conclusion of a spinning process which has produced a large number of bobbins of yarn, the bobbins obtained can be selected on the basis of the breaking tenacity, the modulus or the shrinkage of the material in question.

With the technique according to the invention the Raman spectra can be recorded both during a spinning process and on its conclusion. When the Raman spectra are used to measure the properties of fibres obtained by a spinning process, it is preferred to record them during the spinning process just prior to the fibres being wound or collected, or to record the Raman spectra of the wound/collected fibres.

When the Raman spectra are used to measure properties of fibres at some point during the spinning proces, e.g., when the spectra are used to measure the properties of undrawn fibrous material in a spinning process where the undrawn material is subsequently subjected to drawing, it is preferred to record the Raman spectra during the spinning process, and that at such a point during the spinning process as will give spectra of the undrawn fibres.

The invention will be further illustrated with reference to the following examples. Needless to say, the scope of the invention is not restricted to the specific details of the examples.

EXAMPLES

Example 1

Selected were 60 bobbins containing non-textured polyester textile yarns of differing linear densities prepared by various production processes. A portion of the yarn of each bobbin was used to evaluate the dye uptake using the dye uptake method given in the description. After a portion of the material had been taken off the bobbins, the Raman spectrum of the remaining material was measured by scanning the yarn surface on the bobbin with laser light (power 120 mW) generated with the aid of a Kaiser Holoprobe 785™. A portion of the scattered light was captured and after filtering at 785 nm passed back to the Kaiser Holoprobe 785™ for measuring the Raman spectrum.

The 60 yarn samples further had a number of structural parameters measured. In the set of yarn samples only three of the measured structural parameters were found to vary. Using a statistical analysis of the data the variation in dye uptake by the samples could be traced back to the variation of one principal component. The density of the measured samples was selected for parametrication of this principal component. Using chemometrical techniques, it proved possible with the aid of the Raman spectra to make a very accurate estimate of the density of the samples and thus of their dye uptake. It was also found to be possible to make a very accurate estimate of the dye uptake of textured polyester yarns using the process described above.

Example 2

In an integrated spindrawing process drawn polyester yarns were made from polyester in a known manner. In this process the spinning rate was set at 500, 1150, and 1800 m/min. The spun yarns were drawn in a two-step process. During the drawing the draw ratio was set such that the obtained yarn had an elongation at break of 11, 14 or 17%. Furthermore, the temperature of the godet after the drawing step was set between 205, 225, and 2450° C. In this way 27 different process settings in all were achieved. One situation was repeated three times in the course of the experiment in order to check its reproducibility. In all 30 samples were obtained.

A Raman spectrum was measured on all obtained yarns just upstream of the winder, use being made of a HoloProbe 785 VPT System™ manufactured by Kaiser Optical systems, Inc. The integration time with cosmic ray filtering being switched on was 20 sec., and four measurements were added up to obtain one spectrum. The overall integration time per spectrum thus was 160 s. In each process setting three Raman spectra with a resolution of 4–5 cm$^{-1}$ were recorded. The laser power on the yarn was 70 mW. The laser light was focused with the aid of a lens, and the yarn was passed through the focus of the lens.

All obtained samples had their mechanical properties determined, such as the breaking tenacity (BT), the elongation at break (EaB), the tenacity at specified 2% elongation (TASE 2), and the tenacity at specified 5% elongation (TASE 5). Also determined were such structural parameters as the crystallinity ($V_c$), the average size of the amorphous regions (G), the amorphous orientation factor ($F_{as}$), and the contour length distribution ($F_{ad}=F_{as}/F_{ab}$). For a description of these structural parameters reference is made to H. M. Heuvel, L. J. Lucas, C. J. M. van den Heuvel, and A. P. de Weijer, "Experimental relations between physical structure and mechanical properties of a huge number of drawn poly(ethylene terephthalate) yarns," Journal of Applied Polymer Science, Vol. 45, 1649–1660 (1992).

It was found that all recorded spectra had a signal/noise ratio of more than 2000. The three Raman spectra recorded for each process setting were averaged. These average spectra were used subsequently.

A model was trained on the 30 average spectra using 5-segment cross-validation. To this end the derivative of the spectrum in the region 600–1800 cm$^{-1}$ was determined, followed by MSC (multiple scattering correction), and the surface area of the spectra was standardised. This reduced and scaled spectrum was calibrated with the aid of PLS-1 using 3–4 PLS factors.

Using the model an estimate could be made of the mechanical and structural parameters of the samples, the average deviation of the estimated values for the parameters from the measured parameter values being about equal to the measuring error of the corresponding measured parameters.

In FIG. 1 the breaking tenacity value measured on the respective samples in a load/elongation experiment is plotted against the value determined by means of the Raman spectrum according to the technique described above.

Example 3

The spinning process according to Example 1 was repeated, with the setting of the machine remaining unchanged for six hours. In this way yarn was produced at a spinning rate of 1150 m/min and a temperature of the godet after drawing of 225° C. The yarn had an elongation at break of about 14%.

During the experiment the Raman spectrum of the yarn was measured as described in Example 1, just upstream of the winder. These Raman spectra were treated in the same way as when the model was created in Example 1.

Using this model, the elongation at break during the experiment was determined on the basis of the measured Raman spectra. Subsequently, a number of control measurements were carried out.

Figure 2:
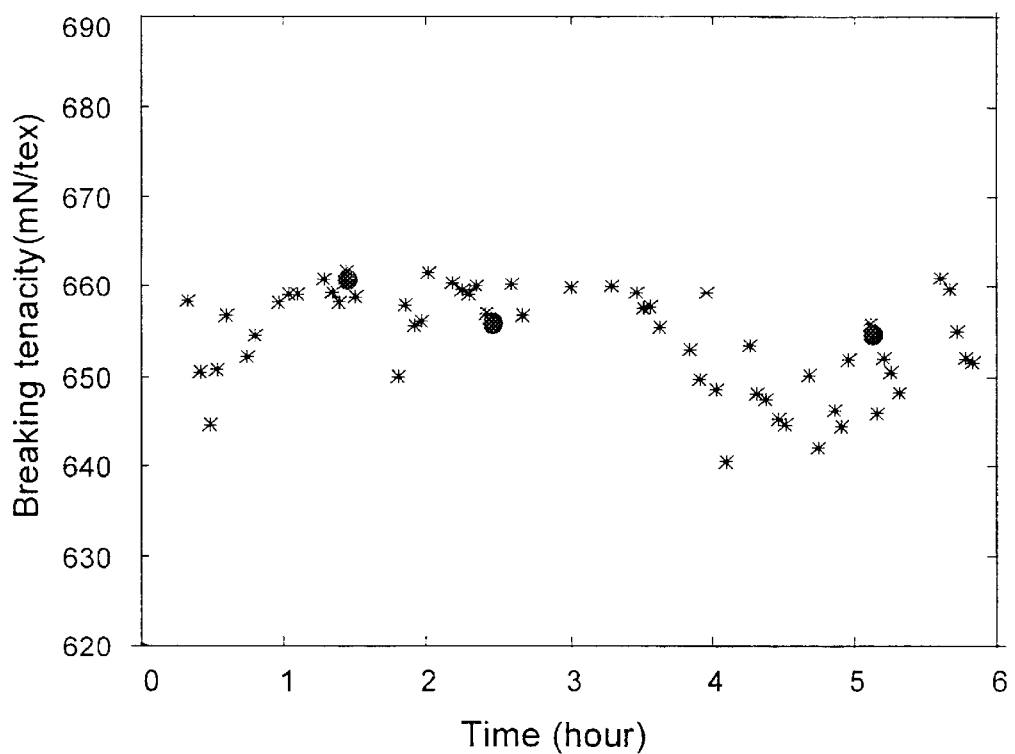
FIG. 2 shows the breaking tenacity calculated from the Raman spectra for the running time of the experiment of Example 3.

FIG. 2 gives the breaking tenacity calculated from the Raman spectra for the running time of the experiment. This figure also shows the control measurement values.

Using Raman spectra, it also proved possible to make an estimate of the shrinkage of a yarn in a comparable manner in a two-step spindrawing process.

What is claimed is:

1. A technique for measuring one or more structural parameters or mechanical properties of polymeric fibers or for determining their dye uptake, said technique comprising the following steps:
 a) creating a model by applying a number of treatment steps, known from the field of chemometrics, to the measured Raman spectrum of a collection of fibrous materials having the same chemical composition as the fibers to be examined, of which the dye uptake, the mechanical or structural properties, and the Raman spectrum are known,
 b) measuring a Raman spectrum of the fibers to be examined by irradiating the fibers with high-intensity monochromatic light, capturing the scattered light, and passing it to a light-sensitive sensor,
 c) treating the measured spectrum obtained in step b), and
 d) applying the model obtained via step a) to the treated spectrum obtained in step c) in order to determine a value of the respective structural parameters or mechanical properties of the fibers to be examined, or to determine their dye uptake.

2. A technique according to claim 1, comprising using the spectral region of 800–2000 $cm^{-1}$ from the Raman spectra for the creation of the model of step a).

3. A technique according to claim 1, wherein the fibers are irradiated with high-intensity monochromatic light generated by a laser.

4. A technique according to claim 1, wherein the monochromatic light has a wavelength in the range of 600 to 900 nm.

5. A technique according to claim 1, wherein each said Raman spectrum has a resolution $\leq 5$ $cm^{-1}$ and a signal/noise ratio $\geq 2000$.

6. A technique according to claim 1, wherein each said Raman spectrum is recorded with a dispersive Raman spectrometer.

7. A technique according to claim 1, wherein the fibers are polyester fibers.

8. A technique according to claim 1, wherein each said Raman spectrum is recorded during a spinning process.

9. A method for selecting or grouping fibers on conclusion of a spinning process, comprising applying the method of claim 1 to fibers exiting a spinning process and selecting or grouping the fibers in response to information determined in step d).

10. A method of adjusting a spinning process, comprising applying the method of claim 1 to fibers exiting a spinning process, and adjusting said spinning process in response to information determined in step d).

* * * * *